United States Patent [19]

Meki et al.

[11] Patent Number: 5,462,961
[45] Date of Patent: Oct. 31, 1995

[54] PYRAZOLE OXIME DERIVATIVES, COMPOSITIONS AND USE

[75] Inventors: Naoto Meki, Kobe; Tomotoshi Imahase, Takarazuka; Kazue Nishida, Tokyo; Hiroaki Fujimoto, Toyonaka; Kenichi Mikitani, Takarazuka; Hirotaka Takano, Sanda; Yoriko Ogasawara, Toyonaka; Masahiro Tamaki, Takarazuka, all of Japan

[73] Assignee: Sumitomo Chemical Company, Limited, Osaka, Japan

[21] Appl. No.: 742,711

[22] Filed: Aug. 5, 1991

Related U.S. Application Data

[63] Continuation of Ser. No. 497,673, Mar. 23, 1990, abandoned.

[30] Foreign Application Priority Data

Mar. 31, 1989 [JP] Japan ........................ 1-82672
Jan. 31, 1990 [JP] Japan ........................ 2-23431

[51] Int. Cl.$^6$ .......................... A01N 43/56; C07D 231/20
[52] U.S. Cl. .......................... 514/407; 548/370.1
[58] Field of Search .................. 548/377, 370.1; 514/407

[56] References Cited

U.S. PATENT DOCUMENTS 4,843,068  6/1989  Hamaguchi et al. ............ 514/63

*Primary Examiner*—Robert W. Ramsuer
*Attorney, Agent, or Firm*—Stevens, Davis, Miller & Mosher

[57] ABSTRACT

The present invention relates to a heterocyclic compound represented by the formula, wherein $R_1$ is a hydrogen atom, or an alkyl or phenyl group; $R_2$ is a hydrogen atom, or an alkyl or haloalkyl group; $R_3$ is a hydrogen atom, or an alkyl or phenyl group, each of $R_4$ and $R_5$, which may be the same or different, is a hydrogen atom or an alkyl group; each of Y's, which may be the same or different, is a hydrogen or halogen atom, or an alkyl, haloalkyl, alkoxyl or haloalkoxyl group; $R_6$ is an alkyl, haloalkyl, alkenyl, haloalkenyl, alkynyl, haloalkynyl, alkoxyalkyl, alkylthioalkyl or cycloalkyl group, or (in which each of V's, which may be the same or different, is a hydrogen or halogen atom, or an alkyl, haloalkyl, alkoxyl or haloalkoxyl group); Z is an oxygen or sulfur atom; and each of m and n is an integer of 1 to 5 and the production method of same. Said compound is useful as an insecticidal, acaricidal and fungicidal agents.

16 Claims, No Drawings

PYRAZOLE OXIME DERIVATIVES, COMPOSITIONS AND USE

This application is a continuation of application Ser. No. 07/497,673, filed Mar. 23, 1990, now abandoned.

The present invention relates to a novel heterocyclic compound, its production, an insecticidal, acaricidal and fungicidal composition containing it as an active ingredient and intermediates for producing it.

EP 234045A$_2$ and Japanese Patent Kokai No. 3086/89 disclose that a certain kind of heterocyclic compounds have an insecticidal, acaricidal and fungicidal activity.

These compounds, however, may not always be said to be satisfactory in terms of the efficacy and spectrum.

In view of such the situation, the present inventors have extensively studied to develop a compound having excellent activities, and have found that a heterocyclic compound represented by the following formula (I) has excellent insecticidal, acaricidal and fungicidal activities. The present inventors have thus completed the present invention.

The present invention provides a heterocyclic compound represented by the formula (I) [hereinafter referred to as present compound(s)], its use, insecticidal, acaricidal and fungicidal compositions containing it as an active ingredient and intermediates for producing it:

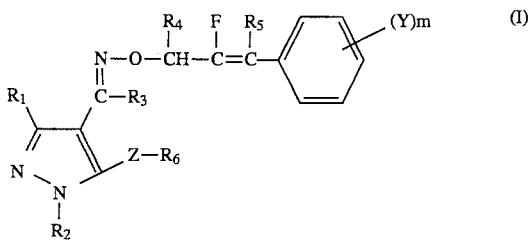

wherein $R_1$ is a hydrogen atom, or an alkyl or phenyl group; $R_2$ is a hydrogen atom, or an alkyl or haloalkyl group; $R_3$ is a hydrogen atom, or an alkyl or phenyl group, each of $R_4$ and $R_5$, which may be the same or different, is a hydrogen atom or an alkyl group; each of Y's, which may be the same or different, is a hydrogen or halogen atom, or an alkyl, haloalkyl, alkoxyl or haloalkoxyl group; $R_6$ is an alkyl, haloalkyl, alkenyl, haloalkenyl, alkynyl, haloalkynyl, alkoxyalkyl, alkylthioalkyl or cycloalkyl group, or

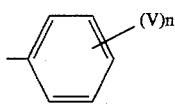

(in which each of V's, which may be the same or different, is a hydrogen or halogen atom, or an alkyl, haloalkyl, alkoxyl or haloalkoxyl group); Z is an oxygen or sulfur atom; and each of m and n is an integer of from 1 to 5.

The formula (I) representing the present compounds will be explained. In $R_1$, the alkyl group is a $C_1$–$C_4$ alkyl group. In $R_2$, the alkyl and haloalkyl groups are a $C_1$–$C_4$ alkyl group and the same group substituted with chlorine, or fluorine, respectively. In $R_3$, the alkyl group is a $C_1$–$C_4$ alkyl group. In $R_4$ and $R_5$, the alkyl group is a $C_1$–$C_4$ alkyl group. In $R_6$, the alkyl, alkenyl and alkynyl groups are those having 1(2) to 10 carbon atoms; the haloalkyl, haloalkenyl groups and haloalkynyl group are those having 1(2) to 10 carbon atoms substituted with a chlorine, bromine or fluorine atom; the alkoxyalkyl is $C_1$–$C_4$ alkoxy $C_2$–$C_8$ alkyl group and alkylthioalkyl is $C_1$–$C_4$ alkylthio $C_2$–$C_8$ alkyl group; the cycloalkyl group is a $C_3$–$C_{10}$ cycloalkyl group. In Y, the halogen atom is a chlorine, bromine or fluorine atom; the alkyl group is a $C_1$–$C_4$ alkyl group; the haloalkyl group is a $C_1$–$C_4$ alkyl group substituted with a chlorine, bromine, or fluorine atom; the alkoxy group is a $C_1$–$C_4$ alkoxyl group; and the haloalkoxyl group is a $C_1$–$C_4$ alkoxyl group substituted with a chlorine, bromine or fluorine atom. In V, the halogen atom is a chlorine, bromine or fluorine atom; the alkyl group is a $C_1$–$C_4$ alkyl group; the haloalkyl group is a $C_1$–$C_4$ alkyl group substituted with a chlorine or fluorine atom; the alkoxyl group is a $C_1$–$C_4$ alkoxyl group; and the haloalkoxyl group is a $C_1$–$C_4$ alkoxyl group substituted with a chlorine or fluorine atom.

Among the present compounds, preferred ones are a compound represented by the formula (I) wherein $R_1$ is a hydrogen atom or an alkyl group; $R_2$ is an alkyl group; $R_3$ is a hydrogen atom or an alkyl group; each of $R_4$ and $R_5$, which may be the same or different, is a hydrogen atom or an alkyl group; each of Y's, which may be the same of different, is a hydrogen or halogen atom, or an alkyl, haloalkyl, alkoxyl or haloalkoxyl group; $R_6$ is an alkyl, haloalkyl, cycloalkyl or alkoxyalkyl group, or

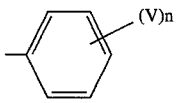

(in which each of V's, which may be the same or different, is a hydrogen or halogen atom, or an alkyl, haloalkyl, alkoxyl or haloalkoxyl group); Z is an oxygen atom; and each of m and n is an integer of 1 or 2.

More preferred compounds are a compound represented by the formula (I) wherein each of $R_1$ and $R_2$ is a methyl group; $R_3$ is a hydrogen atom; each of $R_4$ and $R_5$, which may be the same or different, is a hydrogen atom or a methyl group; each of Y's, which may be the same or different, is a hydrogen or halogen atom, or an alkyl, haloalkyl or haloalkoxyl group; $R_6$ is an alkyl, haloalkyl or cycloalkyl group, or

(in which each of V's, which may be the same or different, is a hydrogen or halogen atom, or an alkyl, haloalkyl or alkoxyl group); Z is an oxygen atom; and each of m and n is an integer of 1 or 2.

Particularly preferred compounds are a compound represented by the formula (I) wherein each of $R_1$ and $R_2$ is a methyl group; $R_3$ is a hydrogen atom; each of $R_4$ and $R_5$ is a hydrogen atom; each of Y's, which may be the same or different, is a hydrogen or halogen atom, or an alkyl or haloalkyl group; $R_6$ is an alkyl, haloalkyl or cycloalkyl group, or

(in which each of V's, which may be the same or different, is a hydrogen or halogen atom); Z is an oxygen atom; and each of m and n is 1.

In the present invention, as illustrative examples the following compounds can be nominated.

1,3-Dimethyl-5-(p-fluorophenoxy)pyrazol-4-carboaldoxime-O-2-fluoro-3-phenyl-2-propenyl ether 1,3-Dimethyl-5-phenoxypyrazol-4-carboaldoxime-O-2-fluoro-3-phenyl-2-propenyl ether 1,3-Dimethyl-5-(p-tert-butylphenoxy)pyrazol-4-carboaldoxime-O-2-fluoro-3-phenyl-2-propenyl ether 1,3-Dimethyl-5-phenoxypyrazol-4-carboaldoxime-O-2-fluoro-3-(p-fluorophenyl)-2-propenyl ether 1,3-Dimethyl-5-phenoxypyrazol-4-carboaldoxime-O-2-fluoro-3-(p-chlorophenyl)-2-propenyl ether 1,3-Dimethyl-5-phenoxypyrazol-4-carboaldoxime-O-2-fluoro-3-(p-trifluoromethylphenyl)-2-propenyl ether 1,3-Dimethyl-5-cyclohexyloxypyrazol-4-carboaldoxime-O-2-fluoro-3-(p-chlorophenyl)-2-propenyl ether 1,3-Dimethyl-5-sec-butyloxypyrazol-4-carboaldoxime-O-2-fluoro-3-(p-chlorophenyl)-2-propenyl ether 1,3-Dimethyl-5-cyclopentyloxypyrazol-4-carboaldoxime-O-2-fluoro-3-(p-chlorophenyl)-2-propenyl ether 1,3-Dimethyl-5-(2,2,2-trifluoroethyloxy) pyrazol-4-carboaldoxime-O-2-fluoro-3-(p-chlorophenyl)-2-propenyl ether.

In the present invention, more preferred compounds include the following:

1,3-Dimethyl-5-phenoxypyrazol-4-carboaldoxime-O-2-fluoro-3-phenyl-2-propenyl ether 1,3-Dimethyl-5-phenoxypyrazol-4-carboaldoxime-O-2-fluoro-3-(p-fluorophenyl)-2-propenyl ether 1,3-Dimethyl-5-phenoxypyrazol-4-carboaldoxime-O-2-fluoro-3-(p-chlorophenyl)-2-propenyl ether 1,3-Dimethyl-5-phenoxypyrazol-4-carboaldoxime-O-2-fluoro-3-(p-trifluoromethylphenyl)-2-propenyl ether 1,3-Dimethyl-5-cyclohexyloxypyrazol-4-carboaldoxime-O-2-fluoro-3-(p-chlorophenyl)-2-propenyl ether 1,3-Dimethyl-5-sec-butyloxypyrazol-4-carboaldoxime-O-2-fluoro-3-(p-chlorophenyl)-2-propenyl ether 1,3-Dimethyl-5-(2,2,2-trifluoroethyloxy) pyrazol-4-carboaldoxime-O-2-fluoro-3-(p-chlorophenyl)-2-propenyl ether.

Insect pests against which the present compounds are efficacious include Hemiptera such as planthoppers, leafhoppers, aphids, bugs, whiteflies, etc.; Lepidoptera such as diamond-back moth (*Plutella xylostella*), rice stem borer (*Chilo suppressalis*), rice leafroller (*Cnaphalocrocis medinalis*), armyworms and cutworms, Plusiid moths (Plusiinae), small white butterfly (*Pieris rapae crucivora*), casemaking clothes moth (*Tinea pellionella*), webbing clothes moth (*Tineola bisselliella*), etc.; Diptera such as common mosquito (*Culex pipiens pallens*), Anopheline mosquito (Anopheles spp.), Aedes mosquito (Aedes spp.), housefly (*Musca domestica*), etc.; Dictyoptera such as German cockroach (*Blattella germanica*), smokybrown cockroach (*Periplaneta fuliqinosa*), brown cockroach (*Periplaneta brunnea*), American cockroach (*Periplaneta americana*), etc.; Coleoptera such as southern corn rootworm, Hymenoptera, Thysanoptera, Orthoptera, etc.; and spider mites such as carmine spider mite (*Tetranychus cinnabarinus*), two-spotted spider mite (*Tetranychus urticae*), citrus red mite (*Panonychus citri*), etc. Further, the present compounds are also efficacious against insect pests having an increased resistance to the existing pesticides.

Further, the present compounds exhibit excellent controlling effects in terms of a preventive effect, a curative effect or a systemic effect on various plant diseases.

As plant diseases on which the present compounds have excellent controlling effect, there are mentioned the following: blast of rice (*Pyricularia oryzae*), helminthosporium leaf spot of rice (*Cochliobolus miyabeanus*), sheath blight of rice (*Rhizoctonia solani*), powdery mildew of wheat & barley (*Erysiphe graminis* f. sp. hordei and E. q. f. sp. tritici), net blotch of wheat & barley (*Pyrenophora teres*), fusarium blight of wheat & barley (*Gibberella zeae*), rust of wheat & barley (*Puccinia striiformis, P. graminis, P. recondita* and *P. hordei*), snow blight of wheat & barley (Typhula sp. and *Micronectriella nivalis*), loose smut of wheat & barley (*Ustilago tritici* and *U. nuda*), bunt of wheat & barley (*Tilletia caries*), eye spot of wheat & barley (*Pseudocercosporella herpotrichoides*), leaf blotch of wheat & barley (*Rhynchosporium secalis*), speckled leaf blotch of wheat & barley (*Septoria tritici*), glume blotch of wheat & barley (*Leptosphaeria nodorum*); melanose of citrus (*Diaporthe citri*), scab of citrus (*Elsinoe fawcetti*), fruit rot of citrus (*Penicillium digitatum* and *P. italicum*); blossom blight of apple (*Sclerotinia mali*), canker of apple (*Valsa mali*), powdery mildew of apple (*Podosphaera leucotricha*), alternaria leaf spot of apple (*Alternaria mali*), scab of apple (*Venturia inaequalis*); scab of pear (*Venturia nashicola* and *V. pirina*), black spot of pear (*Alternaria kikuchiana*), rust of pear (*Gymnosporangium haraeanum*); brown rot of peach (*Sclerotinia cinerea*), scab of peach (*Cladosporium carpophilum*), phomopsis rot of peach (Phomopsis sp.); anthracnose of grape (*Elsinoe ampelina*), ripe rot of grape (*Glomerella cingulata*), powdery mildew of grape (*Uncinula necator*), rust of grape (*Phakopsora ampelopsidis*), black rot of grape (*Guignardia bidwellii*); anthracnose of Japanese persimmon (*Gloeosporium kaki*), leaf spot of Japanese persimmon (*Cercospora kaki* and *Mycosphaerella nawae*): anthracnose of cucumber (*Colletotrichum lagenarium*), powdery mildew of cucumber (*Sphaerotheca fuliqinea*), gummy stem blight of cucumber (*Mycosphaerel molonis*); early blight of tomato (*Alternaria solani*), leaf mold of tomato (*Cladosporium fulvum*); phomopsis blight of eggplant (*Phomopsis vexans*), powdery mildew of eggplant (*Erysiphe cichoracearum*); alternaria leaf spot of brassica (*Alternaria japonica*), white spot of brassica (*Cercosporella brassicae*); rust of Welsh onion (*Puccinia allii*); purple stain of soybean (*Cercospora kikuchii*), anthracnose of soybean (*Elsinoe glycines*), melanose of soybean (*Diaporthe phaseolorum* var. sojae); anthracnose of kidney bean (*Colletotrichum lindemuthianum*); leaf spot of peanut (*Mycosphaerella personatum*), brown leaf spot of peanut (*Cercospora arachidicola*); powdery mildew of pea (*Erysiphe pisi*); early blight of potato (*Alternaria solani*); powdery mildew of strawberry (*Sphaerotheca humuli*); net blister blight of tea (*Exobasidium reticulatum*), white scab of tea (*Elsinoe leucospila*); brown spot of tobacco (*Alternaria longipes*), powdery mildew of tobacco (*Erysiphe cichoracearum*), anthracnose of tobacco (*Colletotrichum tabacum*); cercospora leaf spot of beet (*Cercospora beticola*); scab of rose (*Diplocarpon rosae*), powdery mildew of rose (*Sphaerotheca pannosa*); leaf blight of chrysanthemum (*Septoria chrysanthemi indici*), rust of chrysanthemum (*Puccinia horiana*); gray mold (*Botrytis cinerea*) and stem rot (*Sclerotinia sclerotiorum*) of various crops, and the like.

The present compounds can be produced, for example, by the following methods:

Method A

A method of obtaining the present compounds by reacting a compound represented by the formula (II),

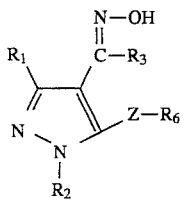 (II)

wherein $R_1$, $R_2$, $R_3$, $R_6$ and Z are as defined above, with a compound represented by the formula (III),

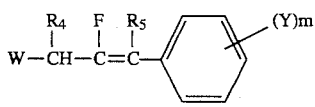 (III)

wherein $R_4$, $R_5$, Y and m are as defined above, and W is a halogen atom.

Method B

A method of obtaining the present compounds by reacting a compound represented by the formula (IV),

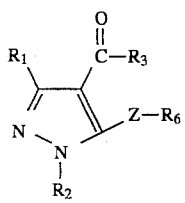 (IV)

wherein $R_1$, $R_2$, $R_3$, $R_6$ and Z are as defined above, with a compound represented by the formula (V),

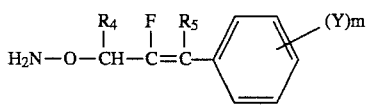 (V)

wherein $R_4$, $R_5$, Y and m are as defined above.

In Method A, a solvent is not always necessary for the reaction, but if necessary, for example, the following solvents may be used: Ethers (e.g. diethyl ether, tetrahydrofuran, dioxane), alcohols (e.g. ethylene glycol, glycerin, methanol, ethanol), acid amides (e.g. N,N-dimethylformamide, N,N-dimethylacetamide), sulfoxides (e.g., sulfolane dimethyl sulfoxide), aromatic hydrocarbons (e.g. benzene, toluene, chlorobenzene), halogenated hydrocarbons (e.g. methylene chloride, chloroform), ketones (e.g. methyl isobutyl ketone), nitriles (e.g. acetonitrile), water and mixtures of these solvents. The compound of the formula (III) is used in an amount of from 0.5 to 10 moles based on 1 mole of the compound of the formula (II). The reaction temperature is usually from −20° to 200° C., preferably from −10° to 100° C. The reaction time is usually from 5 minutes to 100 hours, preferably from 30 minutes to 50 hours.

In carrying out this reaction, usually, the following compounds are used as an acid-binding agent: Alkali metal hydroxides (e.g. lithium hydroxide, sodium hydroxide, potassium hydroxide), alkali metal carbonates (e.g. sodium carbonate, potassium carbonate), alkali metal hydrides (e.g. lithium hydride, sodium hydride, potassium hydride), alkali metals (e.g. metallic lithium, metallic sodium, metallic potassium), alkali metal alkoxides (e.g. sodium methoxide, sodium ethoxide) and mixtures thereof. The amount of the acid-binding agent used is from 0.5 to 10 moles based on 1 mole of the compound of the formula (II). If necessary, as a catalyst for reaction, a phase transfer catalyst such as ammonium salts (e.g. tetra-n-butylammonium bromide, benzyltrimethylammonium chloride), ethers (e.g. 18 -Crown-6), amines [e.g. tris(3,6-dioxaheptyl)amine (TDA- 1)], etc. may be used in an amount of from 0.0001 to 1 mole based on 1 mole of the compound of the formula (II).

After completion of the reaction, the desired present compounds can be obtained by the usual after-treatments such as extraction with an organic solvent, and if necessary, may be purified by chromatography, distillation, recrystallization, etc.

In Method B, a solvent is not always necessary for reaction, but when a solvent is used, for example the following are used: Ethers (e.g. diethyl ether, tetrahydrofuran, dioxane), alcohols (e.g. ethylene glycol, glycerin, methanol, ethanol), acid amides (e.g. N,N-dimethylformamide, N,N-dimethylacetamide), sulfoxides (e.g., sulfolane, dimethyl sulfoxide), aromatic hydrocarbons (e.g. benzene, toluene, chlorobenzene), halogenated hydrocarbons (e.g. methylene chloride, chloroform), aliphatic hydrocarbons (e.g. pentane, hexane, heptane, cyclohexane), pyridines (e.g. pyridine, picoline), acetic acid, water and mixtures of these solvents. The compound of the formula (V) is used in an amount of from 0.5 to 10 moles based on 1 mole of the compound of the formula (IV). The reaction temperature is usually from −20° to 200° C., preferably from −10° to 150° C. The reaction time is usually from 5 minutes to 100 hours, preferably from 5 minutes to 20 hours. If necessary, the following may be used as a catalyst for reaction: Mineral acids (e.g. hydrochloric acid, sulfuric acid, nitric acid), organic acids (e.g. formic acid, acetic acid, propionic acid, methanesulfonic acid, benzenesulfonic acid, p-toluenesulfonic acid), amine/acid adducts (e.g. pyridine hydrochloride, triethylamine hydrochloride, morpholine hydrochloride), etc. The amount of the catalyst used is from 0.001 to 1 mole based on 1 mole of the compound of the formula (IV).

After completion of the reaction, the desired present compounds can be obtained by the usual after-treatments such as extraction with an organic solvent, and if necessary, may be purified by chromatography, distillation, recrystallization, etc.

As examples of the present compound represented by the formula (I), compounds, for example, shown in Table 1 can be mentioned. Of course, however, the present invention is not limited to these examples.

TABLE 1
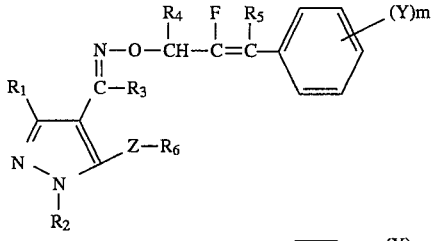
| R₁ | R₂ | R₃ | R₄ | R₅ | Z | 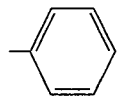 (Y)m | —R₆ |
|---|---|---|---|---|---|---|---|
| H | CH₃ | H | H | H | O | 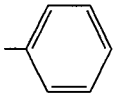 | 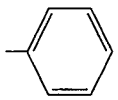 |
| 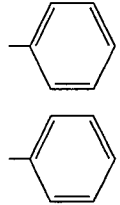 | CH₃ | H | H | H | O | 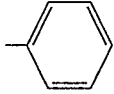 | 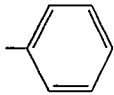 |
| CH₃ | H | H | H | H | O | 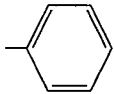 | 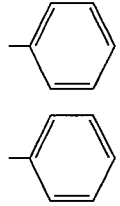 |
| CH₃ | CH₃ | CH₃ | H | H | O | 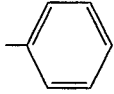 | 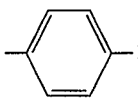 |
| CH₃ | CH₃ | 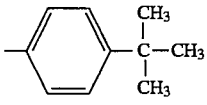 | H | H | O | 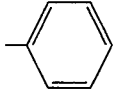 | 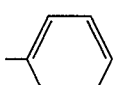 |
| CH₃ | CH₃ | H | CH₃ | H | O | 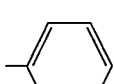 | 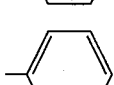 |
| CH₃ | CH₃ | H | H | H | O | | |
| CH₃ | CH₃ | H | H | H | S | | |
| CH₃ | CH₃ | H | H | H | O | | |
| CH₃ | CH₃ | H | H | H | O | | |
| CH₃ | CH₃ | H | H | H | O | | |
| CH₃ | CH₃ | H | H | H | O | | |

TABLE 1-continued

Structure:
$$\underset{R_2}{\underset{|}{N}}\underset{N}{\overset{R_1}{\underset{\|}{C}}}\overset{R_3}{\underset{Z-R_6}{C}}=N-O-\overset{R_4}{\underset{|}{C}H}-\overset{F}{\underset{\|}{C}}=\overset{R_5}{\underset{|}{C}}-\text{Ar}(Y)_m$$

| R₁ | R₂ | R₃ | R₄ | R₅ | Z | ⟨Ph⟩(Y)m | —R₆ |
|---|---|---|---|---|---|---|---|
| CH₃ | CH₃ | H | H | CH₃ | O | phenyl | phenyl |
| CH₃ | CH₃ | H | H | H | O | 4-OCH₃-phenyl | phenyl |
| CH₃ | CH₃ | H | H | H | O | 3-Cl-phenyl | phenyl |
| CH₃ | CH₃ | H | H | H | O | 3-CF₃-phenyl | phenyl |
| CH₃ | CH₃ | H | H | H | O | 4-OCF₂CF₂H-phenyl | phenyl |
| CH₃ | CH₃ | H | H | H | O | 4-OCF₃-phenyl | phenyl |
| CH₃ | CH₃ | H | H | H | O | 4-CF₃-phenyl | 4-Cl-phenyl |
| CH₃ | CH₃ | H | H | H | O | 4-CF₃-phenyl | 3-F-phenyl |
| CH₃ | CH₃ | H | H | H | O | 4-Cl-phenyl | 4-CH₃-phenyl |
| CH₃ | CH₃ | H | H | H | O | 4-Cl-phenyl | 4-CF₃-phenyl |

TABLE 1-continued

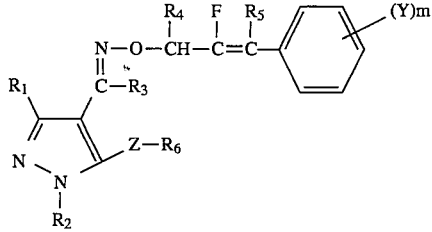

| $R_1$ | $R_2$ | $R_3$ | $R_4$ | $R_5$ | Z | 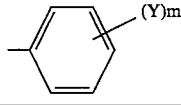 | $-R_6$ |
|---|---|---|---|---|---|---|---|
| $CH_3$ | $CH_3$ | H | H | H | O | 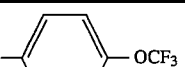 —CF$_3$ | 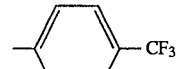 —OCF$_3$ |
| $CH_3$ | $CH_3$ | H | H | H | O | 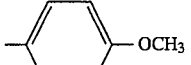 —CF$_3$ | 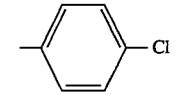 —OCH$_3$ |
| $CH_3$ | $CH_3$ | H | H | H | O | 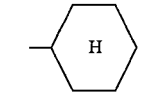 —Cl | 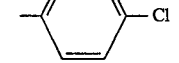 H |
| $CH_3$ | $CH_3$ | H | H | H | O | 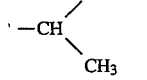 —Cl | —CH(CH$_2$CH$_3$)CH$_3$ |
| $CH_3$ | $CH_3$ | H | H | H | O | 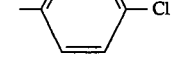 —Cl | 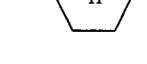 H |
| $CH_3$ | $CH_3$ | H | H | H | O |  —Cl | —CH$_2$CF$_3$ |
| —CH$_2$CH$_3$ | $CH_3$ | H | H | H | O |  —Cl | 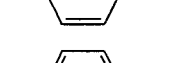 H |
| $CH_3$ | $CH_3$ | H | H | H | O | 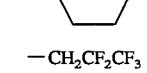 —Cl | —CH$_2$CF$_2$CF$_3$ |
| $CH_3$ | $CH_3$ | H | H | H | O |  —Cl | —CH$_2$CH$_2$CH$_2$CH$_3$ |
| $CH_3$ | $CH_3$ | H | H | H | O | 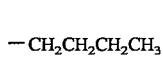 —CF$_3$ |  H |
| $CH_3$ | $CH_3$ | H | H | H | O | 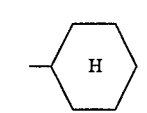 | —CH(CH$_2$CH=CH$_2$)CH$_2$Cl |
| $CH_3$ | $CH_3$ | H | H | H | O | 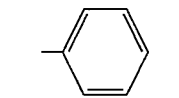 | —CH$_2$CF$_2$CF$_3$ |

TABLE 1-continued

| R₁ | R₂ | R₃ | R₄ | R₅ | Z | (Y)m phenyl | —R₆ |
|---|---|---|---|---|---|---|---|
| CH₃ | CH₃ | H | H | H | O | 4-Cl-phenyl | —CH₂CF₂CF₂CF₃ |
| CH₃ | CH₃ | H | H | H | O | phenyl | —CH₂CH₂CH=CH(CH₃) |
| CH₃ | CH₃ | H | H | H | O | phenyl | —CH₂C≡CCH₃ |
| CH₃ | CH₃ | H | H | H | O | phenyl | —CH(CH₂OCH₃)CH₃ |
| CH₃ | CH₃ | H | H | H | O | phenyl | —CH₂CH₂SCH₃ |
| CH₃ | CH₃ | H | H | H | O | phenyl | —CH(C≡CCH₃)CH₂Cl |
| CH₃ | CH₃ | H | H | H | O | 2,3-diCl-phenyl | phenyl |
| CH₃ | CH₃ | H | H | H | O | 2,4-diCl-phenyl | phenyl |

The compound represented by the formula (V), an intermediate for the present compounds, is a novel compound, and it can be synthesized by the method as described below.

For example, it can be obtained by reacting the compound represented by the formula (III) with a compound represented by the formula (VI),

A—OH  (VI)

wherein A is a group represented by

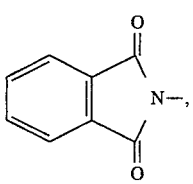

-continued

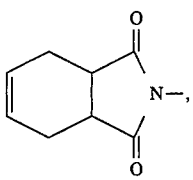

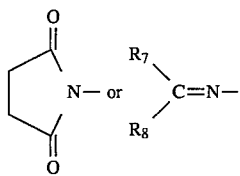

(in which each of $R_7$ and $R_8$, which may be the same or different, is a lower alkyl or phenyl group), to obtain a compound represented by the formula (VII),

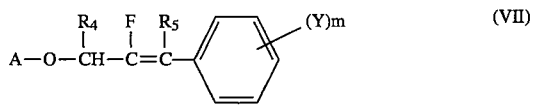   (VII)

wherein $R_4$, $R_5$, A, Y and m are as defined above, and then reacting the resulting compound (VII) with, for example, hydroxylamine or hydrazine, or reacting the resulting compound (VII) with, for example, a mineral acid (e.g. hydrochloric acid, sulfuric acid) and neutralizing the resulting compound.

When the compound of the formula (III) is reacted with the compound of the formula (VI), a solvent is usually used. Such the solvent includes for example amides (e.g. N,N-dimethylformamide, N,N-dimethylacetamide), sulfoxides (e.g. dimethyl sulfoxide, sulfolane), aromatic hydrocarbons (e.g. benzene, toluene, chlorobenzene), halogenated hydrocarbons (e.g. methylene chloride, chloroform, dichloroethane), alcohols (e.g. methanol, ethanol, isopropanol), nitriles (e.g. acetonitrile), water and mixtures thereof. Also, when this reaction is carried out, a base is usually used. Such the base includes for example alkali metal hydroxides (e.g. lithium hydroxide, sodium hydroxide, potassium hydroxide), alkali metal carbonates (e.g. potassium carbonate, sodium carbonate), alkali metal hydrogencarbonates (e.g. sodium hydrogencarbonate), aliphatic amines (e.g. triethylamine), alkali metal alkoxides (e.g. sodium methylate, sodium ethylate), alkali metal hydrides (e.g. sodium hydride, potassium hydride), etc.

As to the amounts of the reagents used for reaction, the amount of the compound of the formula (VI) is from 0.1 to 10 moles, preferably from 0.5 to 2 moles based on 1 mole of the compound of the formula (III), and that of the base is from 0.5 to 10 moles based on the same. The reaction temperature is usually from −30° to 200° C., preferably from −10° to 150° C., and the reaction time is usually from 5 minutes to 100 hours, preferably from 30 minutes to 50 hours.

As an auxiliary for reaction, for example a phase transfer catalyst such as ammonium salts (e.g. tetra-n-butylammonium bromide, benzyltrimethylammonium chloride), ethers (e.g. 18-Crown-6), amines [e.g. tris(3,6-dioxoheptyl)amine (TDA-1)], etc. may be used in an amount of from 0.0001 to 1 mole based on 1 mole of the compound of the formula (III).

After completion of the reaction, the compound represented by the formula (VII) can be obtained by the usual after-treatments such as extraction with an organic solvent, and if necessary, may be purified by chromatography, distillation, recrystallization, etc.

When the compound of the formula (VII) is reacted with hydroxylamine or hydrazine, or with a mineral acid (e.g. hydrochloric acid, sulfuric acid), a solvent is usually used. Such the solvent includes for example alcohols (e.g. methanol, ethanol, isopropanol), aromatic hydrocarbons (e.g. benzene, toluene, chlorobenzene), water and mixtures thereof.

As to the amount of the reagent used for reaction, the amount of hydroxylamine, hydrazine or a mineral acid (e.g. hydrochloric acid, sulfuric acid) is from 0.5 to 100 moles based on 1 mole of the compound of the formula (VII). The reaction temperature is usually from 0° to 300° C., and the reaction time is usually from 5 minutes to 200 hours.

As an auxiliary for reaction, for example a phase transfer catalyst such as ammonium salts (e.g. tetra-n-butylammonium bromide, benzyltrimethylammonium chloride), ethers (e.g. 18-Crown-6), amines [e.g. tris( 3,6-dioxoheptyl)amine (TDA-1)] etc. may be used in an amount of from 0.0001 to 1 mole based on 1 mole of the compound of the formula (VII).

After completion of the reaction, the desired compound of the formula (V) can be obtained by the usual after-treatment of a liquid-liquid separation of the reaction solution, or purification of an acidification and neutralization with an acid (e.g. hydrochloric acid, sulfuric acid) or a base (e.g. sodium hydroxide, potassium hydroxide).

As examples of the compound represented by the formula (V), compounds, for example, shown in Table 2 can be mentioned. Of course, however, the present invention is not limited to these examples.

TABLE 2

$$H_2N-O-\underset{\underset{R_4}{|}}{CH}-\underset{\underset{F}{|}}{C}=\underset{\underset{R_5}{|}}{C}-\text{[phenyl]}-(Y)_m$$

| $R_4$ | $R_5$ | [phenyl]−(Y)m |
|---|---|---|
| H | H | phenyl |
| CH$_3$ | H | phenyl |
| H | H | 4-tert-butylphenyl |
| H | H | 4-fluorophenyl |
| H | H | 4-chlorophenyl |

TABLE 2-continued $$H_2N-O-\underset{\underset{R_4}{|}}{CH}-\underset{\underset{F}{|}}{C}=\underset{\underset{R_5}{|}}{C}-\text{Ar}(Y)_m$$

| $R_4$ | $R_5$ | Aryl |
|---|---|---|
| H | H | -C₆H₄-CF₃ (para) |
| H | CH₃ | -C₆H₅ |
| H | H | -C₆H₄-OCH₃ (para) |
| H | H | -C₆H₄-Cl (meta) |
| H | H | -C₆H₄-CF₃ (meta) |
| H | H | -C₆H₃-Cl,Cl (2,3) |
| H | H | -C₆H₄-OCF₂CF₂ (para) |
| H | H | -C₆H₄-OCF₃ (para) |
| H | H | -C₆H₃-Cl,Cl (2,4) |

The compound represented by the formula (III) can be produced, for example, by the method disclosed in U.S. Pat. No. 4,204,071 or method as described below.

For example, it can be obtained by reacting a compound represented by the formula (VIII), $$R_4-CH=\underset{\underset{F}{|}}{C}-\underset{\underset{O}{\|}}{C}-R_5 \quad \text{(VIII)}$$

wherein $R_4$ and $R_5$ are as defined above, with a compound represented by the formula (IX), $$L-\text{C}_6\text{H}_{4}(Y)_m \quad \text{(IX)}$$

wherein L is a lithium atom, a sodium atom or magnesium halide, and Y and m are as defined above, to obtain a compound represented by the formula (X), $$R_4-CH=\underset{\underset{F}{|}}{C}-\underset{\underset{OH}{|}}{\overset{\overset{R_5}{|}}{C}}-\text{C}_6\text{H}_{4}(Y)_m \quad \text{(X)}$$

wherein $R_4$, $R_5$, Y and m are as defined above, and then subjecting the resulting compound (X) to rearrangement and halogenation.

In the reaction wherein the compound of the formula (VIII) is reacted with the compound of the formula (IX) to obtain the compound of the formula (X), a solvent is usually used. A solvent used includes for example ethers (e.g. diethyl ether, diisopropyl ether, tetrahydrofuran, dioxane), aromatic hydrocarbons (e.g. benzene, toluene, xylene), hydrocarbons (e.g. pentane, hexane, heptane, cyclohexane), and mixtures of these solvents. As to the amount of the reagent used for reaction, the amount of the compound of the formula (IX) is from 0.1 to 10 moles, preferably from 1 to 2 moles based on 1 mole of the compound of the formula (VIII). The reaction temperature is usually from −100° to 300° C., preferably from −50° to 150° C., and the reaction time is usually from 5 minutes to 100 hours, preferably from 30 minutes to 50 hours.

In the reaction wherein the compound of the formula (X) is subjected to rearrangement and halogenation to produce the compound of the formula (III), a solvent may not always be used, but when a solvent is used, for example the following are used: Halogenated hydrocarbons (e.g. methylene chloride, chloroform, dichloroethane), hydrocarbons (e.g. hexane, heptane), aromatic hydrocarbons (e.g. benzene, toluene, chlorobenzene), alcohols (e.g. methanol, ethanol, isopropanol), water and mixtures of these solvents. As the halogenating agent used in this reaction, usual ones such as for example thionyl chloride, phosphorus tribromide, hydrochloric acid, hydrobromic acid, hydroiodic acid, etc. may be used.

As to the amount of the reagent used for reaction, the amount of the halogenating agent is from 0.1 to 10 moles, preferably from 0.5 to 3 moles based on 1 mole of the compound of the formula (X). The reaction temperature is usually from −30° to 200° C., preferably from −20° to 150° C. The reaction time is usually from 5 minutes to 100 hours, preferably from 30 minutes to 50 hours. As an auxiliary for reaction, a compound such as for example amides (e.g. N,N-dimethylformamide), pyridines, anilines (e.g. N,N-dimethylaniline), aliphatic amines (e.g. triethylamine), etc. may be used in an amount of from 0.0001 to 1 mole based on 1 mole of the compound of the formula (X).

After completion of the reaction, the compound represented by the formula (III) can be obtained by the usual after-treatments such as extraction with an organic solvent, and if necessary, may be purified by chromatography, distillation, recrystallization, etc.

The compound represented by the formula (IX) can be obtained, for example, by reacting a compound represented by the formula (XI),

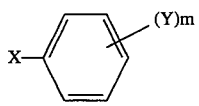

wherein X is a halogen atom, and m and Y are as defined above, with metallic lithium, metallic sodium, metallic magnesium or alkyllithium (e.g. n-butyllithium).

When this reaction is carried out, a solvent is usually used. A solvent used includes for example ethers (e.g. diethyl ether, diisopropyl ether, tetrahydrofuran, dioxane), aromatic hydrocarbons (e.g. benzene, toluene, xylene) and mixtures of these solvents.

As to the amount of the reagent used for reaction, the amount of metallic lithium, metallic sodium, metallic magnesium or alkyllithium (e.g. n-butyllithium) is from 0.1 to 1.5 moles, preferably from 0.8 to 1.3 moles based on 1 mole of the compound of the formula (XI). The reaction temperature is from −100° to 300° C., preferably from −80° to 150° C., and the reaction time is usually from 5 minutes to 100 hours, preferably from 30 minutes to 50 hours.

The compound represented by the formula (VIII) can be produced, for example, by the method described in Synthesis 1985, 755.

The compound represented by the formula (II) or (IV) can be synthesized, for example, by the method disclosed in EP 234045A$_2$ or method described below.

The compound represented by the formula (IV) can be obtained, for example, by reacting a compound represented by the formula (XII),

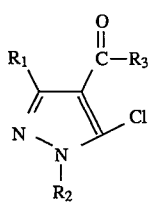

wherein $R_1$, $R_2$ and $R_3$ are as defined above, with a compound represented by the formula (XIII), $R_6$—ZH  (XIII)

wherein $R_6$ and Z are as defined above.

In this reaction, a solvent is not always necessary, but when a solvent is used, for example the following are used: Ethers (e.g. diethyl ether, tetrahydrofuran, dioxane), alcohols (e.g. ethylene glycol, glycerin, methanol, ethanol), acid amides (e.g. N,N-dimethylformamide, N,N-dimethylacetamide), sulfoxides (e.g., sulfolane, dimethyl sulfoxide), aromatic hydrocarbons (e.g. benzene, toluene, chlorobenzene), halogenated hydrocarbons (e.g. methylene chloride, chloroform), pyridines (e.g. pyridine, picoline), water and mixtures of these solvents. The compound of the formula (XIII) is used in an amount of from 0.5 to 10 moles based on 1 mole of the compound of the formula (XII). The reaction temperature is usually from −20° to 200° C., preferably from −10° to 100° C. The reaction time is usually from 5 minutes to 100 hours, preferably from 30 minutes to 50 hours. In carrying out this reaction, usually, the following compounds are used as an acid-binding agent: Alkali metal hydroxides (e.g. lithium hydroxide, sodium hydroxide, potassium hydroxide), alkali metal carbonates (e.g. sodium carbonate, potassium carbonate), alkali metal hydrides (e.g. lithium hydride, sodium hydride, potassium hydride), alkali metals (e.g. metallic lithium, metallic sodium, metallic potassium), alkali metal alkoxides (e.g. sodium methoxide, sodium ethoxide) and mixtures thereof. The amount of the acid-binding agent used is from 0.5 to 10 moles based on 1 mole of the compound of the formula (XII). If necessary, as a catalyst for reaction, a phase transfer catalyst such as ammonium salts (e.g. tetra-n-butylammonium bromide, benzyltrimethylammonium chloride), ethers (e.g. 18-Crown-6), amines [e.g. tris(3,6-dioxaheptyl)amine (TDA-1)], etc. may be used in an amount of from 0.0001 to 1 mole based on 1 mole of the compound of the formula (XII). After completion of the reaction, the desired compound of the formula (IV) can be obtained by the usual after-treatments.

The compound represented by the formula (II) can be obtained, for example, by the method disclosed in EP 234045A$_2$ or method described below.

That is, it can be obtained by reacting the compound of the formula (IV) with a hydroxylamine/acid adduct (e.g. hydroxylamine hydrochloride, hydroxylamine sulfate).

In this reaction, a solvent is not always necessary, but when a solvent is used, for example the following are used: Ethers (e.g. diethyl ether, tetrahydrofuran, dioxane), alcohols (e.g. ethylene glycol, glycerin, methanol, ethanol), acid amides (e.g. N,N-dimethylformamide, N,N-dimethylacetamide), sulfolane, dimethyl sulfoxide, aromatic hydrocarbons (e.g. benzene, toluene, chlorobenzene), halogenated hydrocarbons (e.g. methylene chloride, chloroform), aliphatic hydrocarbons (e.g. pentane, hexane, heptane, cyclohexane), pyridines (e.g. pyridine, picoline), acetic acid, water and mixtures of these solvents. The hydroxylamine/acid adduct is used in an amount of from 0.5 to 10 moles based on 1 mole of the compound of the formula (IV). The reaction temperature is usually from −20° to 200° C., preferably from −10° to 150° C. The reaction time is usually from 5 minutes to 100 hours, preferably from 5 minutes to 20 hours. In carrying out this reaction, usually, the following compounds are used as an acid-binding agent: Alkali metal hydroxides (e.g. lithium hydroxide, sodium hydroxide, potassium hydroxide), alkali metal carbonates (e.g. sodium carbonate, potassium carbonate), alkali metal hydrides (e.g. lithium hydride, sodium hydride, potassium hydride), alkali metals (e.g. metallic lithium, metallic sodium, metallic potassium), alkali metal alkoxides (e.g. sodium methoxide, sodium ethoxide) and mixtures thereof. The amount of the acid-binding agent used is from 0.5 to 10 moles based on 1 mole of the compound of the formula (IV). If necessary, as a catalyst for reaction, a phase transfer catalyst such as ammonium salts (e.g. tetra-n-butylammonium bromide, benzyl-trimethylammonium chloride), ethers (e.g. 18-Crown-6), amines [e.g. tris(3, 6-dioxaheptyl)amine (TDA-1)], etc. may be used in an amount of from 0.0001 to 1 mole based on 1 mole of the compound of the formula (IV).

After completion of the reaction, the desired compound of the formula (II) can be obtained by the usual after-treatments.

When the present compounds are used as an active ingredient for insecticidal, acaricidal and fungicidal compositions, they may be used as they are without adding any other ingredients. Usually, however, they are formulated into oil sprays, emulsifiable concentrates, wettable powders, flowable concentrates, granules, dusts, aerosols, heating fumigants (e.g. mosquito coils, electric mosquito mats), non-heating volatile formulations, smoking formulations, foggings, poisonous baits, etc. by mixing with solid carriers, liquid carriers, gaseous carriers, baits and if necessary, surface active agents and other auxiliaries for formulation.

These preparations contain the present compounds as an active ingredient in an amount of, usually, from 0.01 to 95% by weight.

The solid carriers used in the formulation include, for example, fine powders or granules of clays (e.g. kaolin clay, diatomaceous earth, synthetic hydrated silicon dioxide, bentonite, Fubasami clay, acid clay), talcs, ceramics, other inorganic minerals (e.g. sericite, quartz, sulfur, activated carbon, calcium carbonate, hydrated silica), chemical fertilizers (e.g. ammonium sulfate, ammonium phosphate, ammonium nitrate, urea, ammonium chloride), etc. The liquid carriers include, for example, water, alcohols (e.g. methanol, ethanol), ketones (e.g. acetone, methyl ethyl ketone), aromatic hydrocarbons (e.g. benzene, toluene, xylene, ethylbenzene, methylnaphthalene), aliphatic hydrocarbons (e.g. hexane, cyclohexane, kerosene, gas oil), esters (e.g. ethyl acetate, butyl acetate), nitriles (e.g. acetonitrile, isobutyronitrile), ethers (e.g. diisopropyl ether, dioxane), acid amides (e.g. N,N-dimethylformamide, N,N-dimethylacetamide), halogenated hydrocarbons (e.g. dichloromethane, trichloroethane, carbon tetrachloride), dimethyl sulfoxide, vegetable oils (e.g. soybean oil, cotton seed oil), etc. The gaseous carriers, i.e. a propellant, include, for example, freon gas, butane gas, LPG (liquefied petroleum gas), dimethyl ether, carbon dioxide gas, etc.

The surface active agents used for emulsification, dispersion, wetting, etc. include, for example, anionic surface active agents such as the salt of alkyl sulfates, alkyl(aryl)-sulfonates, dialkyl sulfosuccinates, the salt of polyoxyethylene alkylaryl ether phosphoric acid esters, naphthalenesulfonic acid/formalin condensates, etc., and nonionic surface active agents such as polyoxyethylene alkyl ether, polyoxyethylene polyoxypropylene block copolymers, sorbitan fatty acid esters, polyoxyethylene sorbitan fatty acid esters, etc.

The auxiliaries for formulation such as fixing agents, dispersing agents, etc. include, for example, casein, gelatin, polysaccharides (e.g. starch powder, gum arabic, cellulose derivatives, alginic acid), lignin derivatives, bentonite, saccharides, synthetic water-soluble high polymers (e.g. polyvinyl alcohol, polyvinyl pyrrolidone, polyacrylic acids), etc. The stabilizing agents include, for example, PAP (isopropyl acid phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, surface active agents, fatty acids and their esters, etc.

The base material for mosquito coils includes for example mixtures of a vegetable powder (e.g. wood powder, Pyrethrum marc) with a binder (e.g. Tabu powder, starch, gluten).

The base material for electric mosquito mats includes for example plate-like pressed products of fibrils of cotton linters or a mixture of cotton linters and pulp.

The base material for self-burning-type smoking formulations includes for example burning/heat-generating agents such as nitrates, nitrites, guanidine salts, potassium chlorate, nitrocellulose, ethyl cellulose, wood powders, etc.; pyrolysis-promoting agents such as alkaline earth metal salts, alkali metal salts, dichromates, chromates, etc.; oxygen-supplying agents such as potassium nitrate, etc.; burning-supporting agents such as melamine, wheat starch, etc.; extenders such as diatomaceous earth, etc.; and binders such as synthetic pastes, etc.

The base material for chemical reaction-type smoking formulations includes for example heat-generating agents such as the sulfides, polysulfides, hydrosulfides or salt hydrates of alkali metals, calcium oxide, etc.; catalyzing agents such as carbonaceous substances, iron carbide, activated clay, etc.; organic foaming agents such as azodicarbonamide, benzenesulfonyl hydrazide, dinitrosopentamethylenetetramine, polystyrene, polyurethane, etc.; fillers such as natural fiber pieces, synthetic fiber pieces, etc.

The base material for the non-heating volatile formulations includes for example thermoplastic resins, filter paper, Japanese paper, etc.

The base material for the poisonous baits includes for example bait components (e.g. grain powders, vegetable essential oils, saccharides, crystalline cellulose), antioxidants (e.g. BHT, NDGA, preservatives (e.g. dehydroacetic acid), attractants (e.g. cheese flavor, onion flavor), etc. Further, red pepper powders, etc. also may be included as an agent for preventing children from eating by mistake.

The flowable concentrates (water-based suspension formulations or water-based emulsion formulations) are generally obtained by finely dispersing 1 to 75% of the active ingredient compounds in water containing 0.5 to 15% of a dispersing agent, 0.1 to 10% of a suspension auxiliary (e.g. protective colloids, compounds giving a thixotropic property) and 0 to 10% of a suitable auxiliary (e.g. defoaming agents, anticorrosives, stabilizing agents, spreading agents, penetration auxiliaries, antifreezing agents, antibacterial agents, antimolding agents). It is also possible to obtain oil-based suspension formulations by replacing water by an oil in which the active ingredient compounds are almost insoluble. The protective colloids include for example gelatin, casein, gums, cellulose ethers, polyvinyl alcohol, etc., and the compounds giving a thixotropic property include for example bentonite, aluminum magnesium silicate, xanthane gum, polyacrylic acid, etc.

The preparations thus obtained are used as they are or diluted with water, etc. Further, they may be used together with other insecticides, acaricides, nematocides, soil-pest controlling agents, pest-controlling agents, fungicides, herbicides, plant growth regulators, synergists, fertilizers, soil improvers, etc., or may be used simultaneously with these chemicals without mixing.

When the present compounds are used as an active ingredient for agricultural insecticidal and acaricidal compositions, the dosage rate of the active ingredient is usually from 1 to 1,000 g/10 ares. When the emulsifiable concentrates, wettable powders, flowable concentrates, etc. are used in dilution with water, the application concentration of the active ingredient is usually from 0.1 to 1,000 ppm. The granules, dusts, etc. are used as they are without being diluted. When the present compounds are used as insecticidal and acaricidal compositions for controlling communicable diseases, the emulsifiable concentrates, wettable powders, flowable concentrates, etc. are applied diluted with water to, usually, from 0.1 to 1,000 ppm, and the oil sprays, aerosols, foggings, poisonous baits, etc. are applied as they are.

When the present compounds are used as an active ingredient for fungicidal compositions, the dosage rate of the active ingredient is usually from 1 to 1,000 g/10 ares. When the emulsifiable concentrates, wettable powders, flowable concentrates, etc. are used in dilution with water, the application concentration of the active ingredient is usually from 0.1 to 100,000 ppm. The granules, dusts, etc. are used as they are without being diluted. The present compounds can also be used as seed disinfectants.

Although any of these dosage rate and application concentration varies with the kind of preparations, when, where and how these preparations are applied, the kind of insect pests, the degree of damage, etc., they may be increased or decreased independently of the ranges explained above.

The present invention will be illustrated in more detail with reference to the following production examples, formulation examples and test examples, but it is not limited to these examples.

First, production examples will be shown.

Production Example 1

One gram of 1,3-dimethyl-5-phenoxypyrazol-4-carboaldoxime was added to 10 ml of an N,N-dimethylformamide solution containing 0.11 g of oil dispersed 60% sodium hydride, and the mixture was stirred at room temperature for 3 hours. Thereafter, 0.73 g of 3 -chloro-2-fluoro-1-phenyl-1-pentene was added under ice-cooling, followed by stirring at room temperature for 3 hours. The resulting reaction mixture was poured into 100 ml of ice water, and extracted with three 50-ml portions of ethyl acetate. The organic layers were combined, washed once with 100 ml of a saturated aqueous sodium chloride solution and concentrated under reduced pressure. The residue obtained was subjected to column chromatography on silica gel (eluent, hexane:ethyl acetate=4:1) to obtain 0.25 g of 1,3-dimethyl-5 -phenoxypyrazol-4-carboaldoxime 2-fluoro-3-phenyl-2-pentenyl ether.

$n^{27.9}_D 1.5788$

Production Example 2

One gram of 1,3-dimethyl-5-(cyclohexyloxy)pyrazol-4-carboaldoxime was added to 10 ml of an N,N-dimethylformamide solution containing 0.11 g of oil dispersed 60% sodium hydride, and the mixture was stirred at room temperature for 3 hours. Thereafter, 0.88 g of 3-chloro-2-fluoro-1-(p-chlorophenyl)-1-pentene was added under ice-cooling, followed by stirring at room temperature for 3 hours. The resulting reaction mixture was poured into 100 ml of ice water, and extracted with three 50-ml portions of ethyl acetate. The organic layers were combined, washed once with 100 ml of a saturated aqueous sodium chloride solution and concentrated under reduced pressure. The residue obtained was subjected to column chromatography on silica gel (eluent, hexane:ethyl acetate=4:1) to obtain 0.21 g of 1,3-dimethyl-5-(cyclohexyloxy)pyrazol-4-carboaldoxime 2-fluoro-3-(p-chlorophenyl)-2-pentenyl ether.

$n^{24.6}_D 1.5548$

Production Example 3

One gram of 1,3-dimethyl-5-cyclopentyloxy-pyrazol-4-carboaldehyde was dissolved in 10 ml of ethanol, and to the resulting solution was added 0.97 g of 2-fluoro-3-(p-chlorophenyl)-2-propenyloxyamine. Thereafter, a catalytic amount of a hydrogen chloride gas was bubbled into this reaction solution, and then the solution was aged at room temperature for 10 hours with stirring. After completion of the reaction, the reaction solution was poured into 100 ml of ice water and extracted with two 50-ml portions of ethyl acetate. The organic layers were combined, dehydrated on magnesium sulfate and concentrated under reduced pressure. The residue obtained was subjected to column chromatography on silica gel (eluent, hexane:ethyl acetate=3:1) to obtain 0.21 g of 1,3-dimethyl-5 -cyclopentyloxypyrazol-4-carboaldoxime-O-2-fluoro-3-(p -chlorophenyl)-2-pentenyl ether.

$n^{26.2}_D 1.5676$

Some of the present compounds thus obtained will be shown in Table 3.

TABLE 3

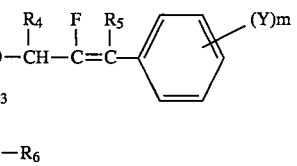

| Compound No. | $R_1$ | $R_2$ | $R_3$ | $R_4$ | $R_5$ | Z | 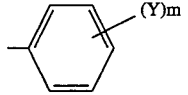 | $-R_6$ | Physical property |
|---|---|---|---|---|---|---|---|---|---|
| (1) | $CH_3$ | $CH_3$ | H | H | H | O | 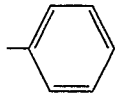 | 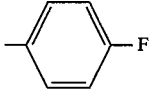 | $n^{26.6}_D 1.5666$ |
| (2) | $CH_3$ | $CH_3$ | H | H | H | S | 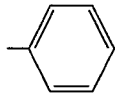 |  | $n^{28.0}_D 1.6039$ |

TABLE 3-continued

[Structure: pyrazole with substituents $R_1$, $R_2$, $R_3$, and $-C(=N-O-CHR_4-CF=CR_5-\text{Ar}(Y)_m)$ group, and $Z-R_6$]

| Compound No. | $R_1$ | $R_2$ | $R_3$ | $R_4$ | $R_5$ | Z | —⟨Ar⟩(Y)m | —$R_6$ | Physical property |
|---|---|---|---|---|---|---|---|---|---|
| (3) | CH₃ | CH₃ | H | H | H | O | -C₆H₄-C(CH₃)₃ | phenyl | $n_D^{26.2}$ 1.5715 |
| (4) | CH₃ | CH₃ | H | H | H | O | -C₆H₄-F | phenyl | $n_D^{23.8}$ 1.5725 |
| (5) | CH₃ | CH₃ | H | H | H | O | -C₆H₄-Cl | phenyl | Glassy |
| (6) | CH₃ | CH₃ | H | H | H | O | -C₆H₄-CF₃ | phenyl | $n_D^{25.1}$ 1.5431 |
| (7) | CH₃ | CH₃ | H | H | H | O | -C₆H₅ | phenyl | $n_D^{27.9}$ 1.5788 |
| (8) | CH₃ | CH₃ | H | H | H | O | -C₆H₄-Cl | cyclohexyl | $n_D^{24.6}$ 1.5548 |
| (9) | CH₃ | CH₃ | H | H | H | O | -C₆H₄-Cl | —CH(CH₂CH₃)CH₃ | $n_D^{25.3}$ 1.5569 |
| (10) | CH₃ | CH₃ | H | H | H | O | -C₆H₄-Cl | cyclopentyl | $n_D^{26.2}$ 1.5676 |
| (11) | CH₃ | CH₃ | H | H | H | O | -C₆H₄-Cl | —CH₂CF₃ | $n_D^{25.7}$ 1.5233 |

Production Example 4

(Production of an intermediate)

One gram of N-hydroxyphthalimide and 1.32 g of 1-bromo-2-fluoro-3-phenyl-2-propene were dissolved in 10 ml of N,N-dimethylformamide at room temperature under a nitrogen atmosphere. To this reaction solution was added 0.85 g of anhydrous potassium carbonate, and then the solution was aged at room temperature for 10 hours with stirring.

The resulting reaction mixture was poured into 100 ml of ice water and extracted with three 50-ml portions of ethyl acetate. The organic layers were combined, washed once with 50 ml of a saturated aqueous sodium chloride solution, dehydrated on anhydrous magnesium sulfate and concentrated under reduced pressure. The residue obtained was washed with hexane to obtain 0.6 g of crude hydroxyphthalimide-O-2-fluoro- 3-phenyl-2-pentenyl ether. Thereafter, 0.5 g of this crude hydroxyphthalimide-O-2-fluoro-3-phenyl-2-pentenyl ether was dissolved in 20 ml of toluene. To the resulting solution were added 2.69 ml of a 5% aqueous sodium hydroxide solution, 0.12 g of hydroxylamine hydrochloride and 27 mg of tetra-n-butylammonium bromide, and then stirring was continued at room temperature for 10 hours. The aqueous layer was removed by liquid-liquid separation, and the toluene layer was washed once with 20 ml of a saturated aqueous sodium chloride solution, then dehydrated on anhydrous magnesium sulfate and concentrated under reduced pressure. The residue obtained was subjected to column chromatography on silica gel (eluent, hexane:ethyl acetate=3:1) to obtain 0.11 g of hydroxylamine-O-2-fluoro-3-phenyl-2-propenyl ether.

m.p. 41.3° C.

Formulation examples will be shown. In the examples, parts are by weight, and the present compounds used for test are shown by Compound Nos. in Table 3.

Formulation Example 1

Ten parts of each of the present compounds (1) to (11), 35 parts of xylene, 35 parts of dimethylformamide, 14 parts of polyoxyethylene styrylphenyl ether and 6 parts of calcium dodecylbenzenesulfonate are well stirred and mixed to obtain a 10% emulsifiable concentrate of each compound.

Formulation Example 2

Twenty parts of the present compound (1) is added to a mixture comprising 4 parts of sodium lauryl sulfate, 2 parts of calcium lignosulfonate, 20 parts of synthetic hydrated silicon dioxide fine powders and 54 parts of diatomaceous earth. The resulting mixture is stirred and mixed on a juice mixer to obtain a 20% wettable powder.

Formulation Example 3

To 5 parts of the present compound (1) are added 5 parts of synthetic hydrated silicon dioxide fine powders, 5 parts of sodium dodecylbenzenesulfonate, 30 parts of bentonite and 55 parts of clay, and the resulting mixture is well stirred and mixed. A suitable amount of water is added to this mixture, and the mixture is further stirred, granulated on a granulator and air-dried to obtain a 5% granule.

Formulation Example 4

One part of each of the present compounds (1) to (11) is dissolved in a suitable amount of acetone, and to the resulting solution are added 5 parts of synthetic hydrated silicon dioxide fine powders, 0.3 part of PAP and 93.7 parts of clay. The mixture is stirred and mixed on a juice mixer. Thereafter, acetone is removed by vaporization to obtain a 1% dust of each compound.

Formulation Example 5

Twenty parts of the present compound (1) and 1.5 parts of sorbitan trioleate are mixed with 28.5 parts of an aqueous solution containing 2 parts of polyvinyl alcohol, and the mixture is finely pulverized to a particle size of 3 μ or less on a sand grinder. Thereafter, 40 parts of an aqueous solution containing 0.05 part of xanthane gum and 0.1 part of aluminum magnesium silicate is added, and then 10 parts of propylene glycol is additionally added. The resulting mixture is stirred and mixed to obtain a 20% flowable formulation (water-based suspension formulation).

Formulation Example 6

0.1 Part of the present compound (1) is dissolved in a mixture of 5 parts of xylene and 5 parts of trichloroethane. The resulting solution is mixed with 89.9 parts of deodorized kerosene to obtain a 0.1% oil spray.

Test examples will be shown. The present compounds used for test are shown by Compound Nos. in Table 3, and compounds used as a reference are shown by Compound symbols in Table 4.

TABLE 4

| Compound Symbol | Structural formula | Remarks |
| --- | --- | --- |
| (A) | [pyrazole with CH₃, CH=NO—CH₃, O-phenyl, N-CH₃ substituents] | Compound No. 790 described in EP 234045A₂. |
| (B) | [morpholine derivative with H₃C, H₃C, O, N—C₁₃H₂₇] | Tridemorph (commercially available fungicide). |
| (C) | [pyrazole with CH₃, CH=NOCH₂CH=CH-phenyl-Cl, O-phenyl, N-CH₃ substituents] | Compound No. 845 described in EP 234045A₂. |

That the present compounds are efficacious as an insecticidal and acaricidal composition will be proved by the following test examples.

Test example 1 Insecticidal test on tobacco cutworm (*Spodoptera litura*)

Each test compound was formulated into an emulsifiable concentrate according to Formulation example 1, and 2 ml of the 200-fold aqueous dilute solution (500 ppm) of the emulsifiable concentrate was impregnated into 13 g of artificial feeds for tobacco cutworm previously prepared in a polyethylene cup of 11 cm in diameter. Ten fourth instar larvae of tobacco cutworm were liberated in the cup. After six days, the dead and alive of the larvae were examined to obtain a mortality. At the same time, the degree of attack upon the artificial feeds was also examined. The degree of attack was judged based on the following standard:

−: Little attack is observed.
+: Attack is observed.
++: Attack is heavy, few artificial feeds being left. The results are shown in Table 5.

TABLE 5

| Test compound | Mortality (%) | Degree of attack |
|---|---|---|
| (1) | 100 | − |
| (4) | 100 | − |
| (5) | 100 | − |
| (6) | 100 | − |
| (7) | 100 | − |
| (8) | 100 | − |
| (10) | 100 | − |
| (A) | 10 | ++ |
| No treatment | 0 | ++ |

Test example 2 Insecticidal test on common mosquito larvae (*Culex pipiens pallens*)

The emulsifiable concentrate of each test compound prepared according to Formulation example 1 was diluted with water so that the active ingredient concentration was 3.5 ppm. 100 ml of the resulting dilute solution was put in a 180-ml polyethylene cup, and 20 last instar larvae of common mosquito were liberated in the solution. After one day, the mortality of the larvae was examined. The mortality was indicated in the following three stages.

Mortality a: Not less than 90%
Mortality b: Less than 90% to 10%
Mortality c: Less than 10%
The results are shown in Table 6.

TABLE 6

| Test compound | Mortality |
|---|---|
| (1) | a |
| (3) | b |
| (4) | a |
| (5) | a |
| (6) | a |
| (7) | a |
| (8) | a |
| (9) | a |
| (10) | a |
| (11) | a |
| (A) | c |
| No treatment | c |

Test example 3 Acaricidal test on carmine spider mite (*Tetranychus cinnabarinus*)

The female adults of carmine spider mite were parasitized, at a rate of 10 adults/leaf, on potted kidney bean (in the primary leaf stage) which had elapsed 7 days after seeding, and placed in a greenhouse kept at 25°–28° C. After 6 days, the emulsifiable concentrate of each test compound prepared according to Formulation example 1 was diluted 200 times with water (active ingredient concentration, 500 ppm), and this 200-fold aqueous dilute solution was sprayed onto the plant at a rate of 15 ml/pot on a turn table. At the same time, the soil was drenched with 2 ml of the same dilute solution. After 8 days, the degree of damage of each plant by the mite was examined. The standard for judging the effect was as follows:

−: Little damage is observed.
+: Slight damage is observed.
++: Same damage as in the untreated plot is observed.
The results are shown in Table 7.

TABLE 7

| Test compound | Degree of damage |
|---|---|
| (1) | − |
| (2) | + |
| (3) | + |
| (4) | + |
| (5) | − |
| (6) | − |
| (7) | − |
| (8) | − |
| (9) | − |
| (10) | − |
| (11) | + |
| (A) | + |
| No treatment | ++ |

Test example 4 Insecticidal test on housefly (*Musca domestica*)

On the bottom of a polyethylene cup of 5.5 cm in diameter was placed a filter paper of the same size as the bottom. Separately from this, the emulsifiable concentrate of each test compound prepared according to Formulation example 1 was diluted 200 times with water (active ingredient concentration, 500 ppm), and 0.7 ml of this 200-fold aqueous dilute solution was dropped down to the filter paper. About 30 mg of sucrose was uniformly placed as a bait on the filter paper, and 10 female adults of housefly were liberated in the cup. Twenty-four hours after covering the cup, the dead and alive of the adults were examined to obtain a mortality. This test was repeated twice. The results are shown in Table 8.

TABLE 8

| Test compound | Mortality (%) |
|---|---|
| (1) | 100 |
| (4) | 100 |
| (5) | 100 |
| (6) | 100 |
| (7) | 100 |
| No treatment | 0 |

Test example 5 Insecticidal test on brown plant-hopper (*Nilaparvata lugens*)

Each test compound was formulated into an emulsifiable concentrate according to Formulation example 1, and rice stems (length, about 12 cm) were dipped for 1 minute in the 200-fold aqueous dilute solution (active ingredient concentration, 500 ppm) of the emulsifiable concentrate. After air-drying, the rice stems were put in a test tube, and 20 first to second instar larvae of brown planthopper were liberated in the test tube. After six days, the dead and alive of the larvae were examined to obtain a mortality. The mortality was indicated in the following three stages.

Mortality a: Not less than 90%
Mortality b: Less than 90% to not less than 80%
Mortality c: Less than 80%
The results are shown in Table 9.

TABLE 9

| Test compound | Mortality |
|---|---|
| (5) | a |
| (6) | b |
| (8) | a |
| (9) | a |
| (10) | a |
| (11) | a |
| No treatment | c |

Test example 6 Insecticidal test on southern corn rootworm (*Diabrotica undecimpunctata howardi* Harber)

On the bottom of a polyethylene cup of 5.5 cm in diameter was placed a filter paper of the same size as the bottom. Separately from this, the emulsifiable concentrate of each test compound prepared according to Formulation example 1 was diluted 2000 times with water (active ingredient concentration, 50 ppm), and 1 ml of this 2000-fold aqueous dilute solution was dropped down to the filter paper. Thereafter, 20 to 30 eggs of southern corn rootworm and one piece of germinated corn were put in the cup which was then covered. After eight days, the dead and alive of the larvae and the degree of attack upon the corn were examined. The standard for judging the effect was as follows:

| Mortality | Degree of attack |
|---|---|
| A: 100% | −: No attack |
| B: Less than 100% to not less than 90% | ±: Slight attack |
|  | ++: Same attack as in the untreated plot. |

C: Less than 90%
The results are shown in Table 10.

TABLE 10

| Test compound | Mortality | Degree of attack |
|---|---|---|
| (1) | A | ± |
| (4) | A | − |
| (5) | A | − |
| (8) | A | − |
| (9) | A | − |
| (C) | C | ++ |
| No treatment | C | ++ |

The present compounds are effective as a fungicidal composition will be proved by the following test examples.

The controlling activity was evaluated in six stages described below, 5, 4, 3, 2, 1 and 0, by macroscopically observing the condition of disease of the test plants, i.e. the degrees of colony and infected area on the leaves, stems, etc., at the time of examination.
5 Colony or infected area is not observed at all.
4 About 10% of colony or infected area is observed.
3 About 30% of colony or infected area is observed.
2 About 50% of colony or infected area is observed.
1 About 70% of colony or infected area is observed.
0 More than about 70% of colony or infected area is observed, there being no difference in the condition of disease between the treated and untreated plots.

Test example 7 Controlling test on blast of rice (*Pyricularia oryzae*) (preventive effect)

Sandy loam was filled in plastic pots, and rice (var., Kinki No. 33) was sowed and cultivated for 20 days in a greenhouse to obtain rice seedlings. The emulsifiable concentrates of the test compounds obtained according to Formulation example 1 were each diluted with water to a prescribed concentration and foliar-applied onto the seedlings so that the spray liquor thoroughly adhered to the leaf surface. After the spraying, the seedlings were air-dried and inoculated by spraying the spore suspension of *Pyricularia oryzae*. After the inoculation, the seedlings were placed for 8 days in a greenhouse of 26 C which was brought to a highly humid condition only during the night. The controlling activity was then examined.

The results are shown in Table 11.

TABLE 11

| Test compound | Concentration (ppm) | Controlling activity |
|---|---|---|
| (1) | 200 | 5 |
|  | 50 | 5 |
| (4) | 200 | 5 |
| (B) | 200 | 0 |

Test example 8 Controlling test on powdery mildew of wheat (*Erysiphe graminis* f. sp. tritici) (curative effect)

Sandy loam was filled in plastic pots, and wheat (var., Norin No. 73) was sowed and cultivated for 10 days in a greenhouse to obtain wheat seedlings. The seedlings were inoculated with *Erysiphe graminis* f. sp. tritici. After the inoculation, the seedlings were cultivated at 15° C. for 2 days. Thereafter, the emulsifiable concentrates of the test compounds obtained according to Formulation example 1 were each diluted with water to a given concentration and foliar-applied onto the seedlings so that the spray liquor thoroughly adhered to the leaf surface. After the spraying, the seedlings were cultivated for 7 days in a growth room of 15° C., and the controlling activity was then examined. The results are shown in Table 12.

Test example 9 Controlling test on glume blotch of wheat (*Leptosphaeria nodorum*) (preventive effect)

Sandy loam was filled in plastic pots, and wheat (var., Norin No. 73) was sowed and cultivated for 8 days in a greenhouse to obtain wheat seedlings. The emulsifiable concentrates of the test compounds obtained according to Formulation example 1 were each diluted with water to a given concentration and foliar-applied onto the seedlings so that the spray liquor thoroughly adhered to the leaf surface. After the spraying, the seedlings were air-dried and inoculated by spraying the spore suspension of *Leptosphaeria nodorum*. After the inoculation, the seedlings were kept for 1 day at 15° C. under a dark and highly humid condition, and then cultivated at 15° C. for 10 days under lighting. The controlling activity was then examined. The results are shown in Table 12.

Test example 10 Controlling test on net blotch of barley (*Pyrenophora teres*) (preventive effect)

Sandy loam was filled in plastic pots, and barley (var., Akashinriki) was sowed and cultivated for 14 days in a greenhouse to obtain barley seedlings. The emulsifiable concentrates of the test compounds obtained according to Formulation example 1 were each diluted with water to a given concentration and foliar-applied onto the seedlings so that the spray liquor thoroughly adhered to the leaf surface. After the spraying, the seedlings were air-dried and inoculated by spraying the spore suspension of *Pyrenophora teres*. After the inoculation, the seedlings were kept for 3 days at 15° C. under a dark and highly humid condition, and then cultivated at 20° C. for 14 days under lighting. The controlling activity was then examined. The results are shown in Table 12.

Test example 11 Controlling test on leaf blotch of barley (*Rhynchosporium secalis*) (preventive effect)

Sandy loam was filled in plastic pots, and barley (var., Akashinriki) was sowed and cultivated for 14 days in a greenhouse to obtain barley seedlings. The emulsifiable concentrates of the test compounds obtained according to Formulation example 1 were each diluted with water to a given concentration and foliar-applied onto the seedlings so that the spray liquor thoroughly adhered to the leaf surface. After the spraying, the seedlings were air-dried and inoculated by spraying the spore suspension of *Rhynchosporium secalis*. After the inoculation, the seedlings were kept for 1 day at 15° C. under a dark and highly humid condition, and then cultivated at 20° C. for 14 days under lighting. The controlling activity was then examined. The results are shown in Table 12.

Test example 12 Controlling test on leaf rust of wheat (*Puccinia recondita*) (preventive effect)

Sandy loam was filled in plastic pots, and wheat (var., Norin No. 73) was sowed and cultivated for 14 days in a greenhouse to obtain wheat seedlings. The emulsifiable concentrates of the test compounds obtained according to Formulation example 1 were each diluted with water to a given concentration and foliar-applied onto the seedlings so that the spray liquor thoroughly adhered to the leaf surface. After the spraying, the seedlings were air-dried and inoculated with the spores of *Puccinia recondita*. After the inoculation, the seedlings were kept for 1 day at 23° C. in a dark and humid room and then cultivated for 10 days under lighting. The controlling activity was then examined. The results are shown in Table 12.

TABLE 12

| Test compound | Concentration (ppm) | Controlling activity | | | | |
|---|---|---|---|---|---|---|
| | | Powdery mildew of wheat | Glume blotch of wheat | Net blotch of barley | Leaf blotch of barley | Leaf rust of wheat |
| (1) | 400 | 5 | 3 | 5 | 0 | 5 |
| (4) | 400 | 5 | 4 | 5 | 4 | 5 |
| (B) | 400 | 5 | 0 | 0 | 2 | 3 |
| (C) | 400 | 0 | 0 | 0 | 0 | 0 |

Test example 13 Controlling test on late blight of tomato (*Phytophthora infestans*) (preventive effect)

Sandy loam was filled in plastic pots, and tomato (var., Ponteroza) was sowed and cultivated for 20 days in a greenhouse to obtain tomato seedlings in the second to third leaf stage. The wettable powders of the test compounds obtained according to Formulation example 2 were each diluted with water to a prescribed concentration and foliar-applied onto the seedlings so that the spray liquor thoroughly adhered to the leaf surface. After the spraying, the seedlings were inoculated by spraying the spore suspension of *Phytophthora infestans*. After the inoculation, the seedlings were kept for 1 day at 20° C. under a highly humid condition and then cultivated for 5 days under lighting. The controlling activity was then examined. The results are shown in Table 13.

TABLE 13

| Test compound | Concentration (ppm) | Controlling activity |
|---|---|---|
| (1) | 400 | 4 |
| | 50 | 4 |
| (4) | 400 | 5 |
| | 50 | 4 |
| (7) | 400 | 4 |
| (8) | 400 | 4 |
| (B) | 400 | 0 |

Test example 14 Controlling test on downy mildew of cucumber (*Pseudoperonospora cubensis*) (curative effect)

Sandy loam was filled in plastic pots, and cucumber (var., Sagamihanjiro) was sowed and cultivated for 14 days in a greenhouse to obtain cucumber seedlings in the cotyledonous stage. The seedlings were inoculated by spraying the spore suspension of *Pseudoperonospora cubensis*. After the inoculation, the seedlings were kept for 1 day at 20° C. under a highly humid condition. Thereafter, the wettable powders of the test compounds obtained according to Formulation example 2 were each diluted with water to a prescribed concentration and foliar-applied onto the seedlings so that the spray liquor thoroughly adhered to the leaf surface. After the spraying, the seedlings were cultivated for 8 days under lighting, and then the controlling activity was examined. The results are shown in Table 14.

TABLE 14

| Test compound | Concentration (ppm) | Controlling activity |
|---|---|---|
| (1) | 400 | 4 |
| (3) | 400 | 4 |
| (4) | 400 | 5 |
| (7) | 400 | 5 |
| (8) | 400 | 4 |
| (9) | 400 | 5 |
| (10) | 400 | 5 |
| (B) | 400 | 0 |

Test example 15 Controlling test on alternaria spot of Japanese radish (*Alternaria brassicicola*) (preventive effect)

Sandy loam was filled in plastic pots, and Japanese radish (var., 60-Nichi daikon) was sowed and cultivated for 6 days in a greenhouse to obtain Japanese radish seedlings in the cotyledonous stage. The wettable powders of the test compounds obtained according to Formulation example 2 were each diluted with water to a prescribed concentration and foliar-applied onto the seedlings so that the spray liquor thoroughly adhered to the leaf surface. After the spraying, the seedlings were inoculated by spraying the spore suspension of *Alternaria brassicicola*. After the inoculation, the seedlings were kept for 1 day at 18° C. under a highly humid condition and then cultivated for 3 days under lighting. The controlling activity was then examined. The results are shown in Table 15.

TABLE 15

| Test compound | Concentration (ppm) | Controlling activity |
|---|---|---|
| (1) | 400 | 5 |
| | 50 | 5 |
| (4) | 400 | 5 |
| | 50 | 5 |
| (7) | 400 | 5 |
| (8) | 400 | 4 |

TABLE 15-continued

| Test compound | Concentration (ppm) | Controlling activity |
| --- | --- | --- |
| (B) | 400 | 2 |
| (C) | 400 | 0 |

Effect of the Invention

The present compounds have excellent insecticidal activity against insect pests belonging to Hemiptera, Lepidoptera, Diptera, Dictyoptera, Coleoptera, Hymenoptera, Thysanoptera, Orthoptera and Acarina. Also, they have not only a preventive effect, but also a high curative effect on various plant diseases, as well as a broad antimicrobial spectrum. Consequently, the present compounds can be used in various applications as an active ingredient for insecticidal, acaricidal and fungicidal compositions.

What is claimed is:

1. A heterocyclic compound represented by the formula,

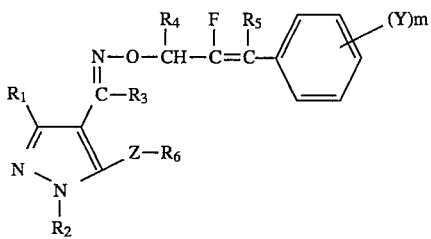

wherein $R_1$ is hydrogen, $C_1$–$C_4$ alkyl or phenyl; $R_2$ is hydrogen or $C_1$–$C_4$ haloalkyl; $R_3$ is hydrogen, $C_1$–$C_4$ alkyl or phenyl; each of $R_4$ and $R_5$, which may be the same or different, is hydrogen or $C_1$–$C_4$ alkyl; each of Y's, which may be the same or different, is hydrogen, halogen, $C_1$–$C_4$ alkyl, $C_1$–$C_4$ haloalkyl, $C_1$–$C_4$ alkoxy or $C_1$–$C_4$ haloalkoxy; $R_6$ is $C_1$–$C_{10}$ alkyl, $C_2$–$C_0$ haloalkyl, $C_2$–$C_{10}$ alkenyl, $C_2$–$C_{10}$ haloalkenyl, $C_2$–$C_{10}$ alkynyl, $C_2$–$C_{10}$ haloalkynyl, $C_1$–$C_4$ alkoxy $C_2$–$C_8$ alkyl, $C_1$–$C_4$ alkyl $C_2$–$C_8$ thioalkyl, $C_3$–$C_{10}$ cycloalkyl or

(in which each of V's, which may be the same or different, is hydrogen, halogen, $C_1$–$C_4$ alkyl, $C_1$–$C_4$ haloalkyl, $C_1$–$C_4$ alkoxy or $C_1$–$C_4$ haloalkoxy); Z is oxygen or sulfur; and each of m and n is an integer of 1 to 5.

2. A heterocyclic compound represented by the formula,

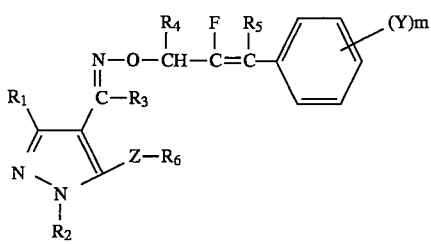

wherein $R_1$ is hydrogen, $C_1$–$C_4$ alkyl or phenyl; $R_2$ is $C_1$–$C_4$ alkyl; $R_3$ is hydrogen, $C_1$–$C_4$ alkyl or phenyl; each of $R_4$ and $R_5$, which may be the same or different, is hydrogen or $C_1$–$C_4$ alkyl; each of Y's, which may be the same or different, is hydrogen, halogen, $C_1$–$C_4$ alkyl, $C_1$–$C_4$ haloalkyl, $C_1$–$C_4$ alkoxy or $C_1$–$C_4$ haloalkoxy; $R_6$ is $C_1$–$C_{10}$ alkyl, $C_1$–$C_{10}$ haloalkyl, $C_2$–$C_{10}$ alkenyl, $C_2$–$C_{10}$ haloalkenyl, $C_2$–$C_{10}$ alkynyl, $C_2$–$C_{10}$ haloalkynyl, $C_1$–$C_4$ alkoxy $C_2$–$C_8$ alkyl, $C_1$–$C_4$ alkyl $C_2$–$C_8$ thioalkyl, $C_3$–$C_{10}$ cycloalkyl or

(in which each of V's, which may be the same or different, is hydrogen, halogen, $C_1$–$C_4$ alkyl, $C_1$–$C_4$ haloalkyl, $C_1$–$C_4$ alkoxy or $C_1$–$C_4$ haloalkoxy); Z is oxygen or sulfur; and each of m and n is an integer of 1 to 5.

3. A heterocyclic compound according to claim 1 or 2, wherein $R_1$ is a hydrogen atom or an alkyl group; $R_2$ is an alkyl group; $R_3$ is a hydrogen atom or an alkyl group; each of $R_4$ and $R_5$, which may be the same or different, is a hydrogen atom or an alkyl group; each of Y's is a hydrogen or halogen atom, or an alkyl, haloalkyl, alkoxyl or haloalkoxyl group; $R_6$ is an alkyl, haloalkyl, cycloalkyl or alkoxyalkyl group, or

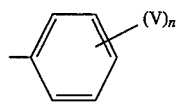

(in which each of V's is a hydrogen or halogen atom, or an alkyl, haloalkyl, alkoxyl or haloalkoxyl group); Z is an oxygen atom; and each of m and n is an integer of 1 or 2.

4. A heterocyclic compound according to claim 3, wherein each of $R_1$ and $R_2$ is a methyl group; $R_3$ is a hydrogen atom; each of $R_4$ and $R_5$ which may be the same or different, is a hydrogen atom or a methyl group; each of Y's is a hydrogen or halogen atom, or an alkyl or haloalkoxyl group; $R_6$ is an alkyl, haloalkyl or cycloalkyl group, or

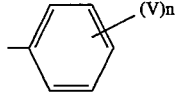

(in which each of V's is a hydrogen or halogen atom, or an alkyl, haloalkyl or alkoxyl group).

5. A heterocyclic compound according to claim 4, wherein each of $R_4$ and $R_5$ is a hydrogen atom; each of Y's is a hydrogen or halogen atom, or an alkyl or haloalkyl group; $R_6$ is an alkyl, haloalkyl or cycloalkyl group, or

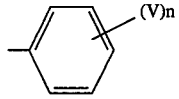

(in which each of V's is a hydrogen or halogen atom); and each of m and n is 1.

6. A heterocyclic compound according to claim 1 or 2 selected from a group of the following compounds:

1,3-dimethyl-5-(p-fluorophenoxy)pyrazol-4 -carboaldoxime-O-2-fluoro-3-phenyl-2-propenyl ether, 1,3-dimethyl-5-phenoxypyrazol-4-carboaldoxime -O-2- fluoro-3-phenyl-2-propenyl ether, 1,3-dimethyl-5-(p-tert-butylphenoxy)pyrazol-4 -carboaldoxime-O-2-fluoro-3-phenyl-2-propenyl ether, 1,3-dimethyl-5-phenoxypyrazol-4-carboaldoxime -O-2-fluoro-3-(p-fluorophenyl)-2-propenyl ether, 1,3-dimethyl-5-phenoxypyrazol-4-carboaldoxime -O-2-fluoro-3-(p-chlorophenyl)-2-propenyl ether, 1,3-dimethyl-5-phenoxypyrazol-4-carboaldoxime -O-2-fluoro-3-(p-trifluoromethylphenyl)-2-propenyl ether, 1,3-dimethyl-5-cyclohexyloxypyrazol-4 -O-carboaldoxime-O-2-fluoro-3-(p-chlorophenyl)-2-propenyl ether, 1,3-dimethyl-5-sec-butyloxypyrazol-4 -O-carboaldoxime-O-2-fluoro-3-(p-chlorophenyl)-2-propenyl ether, 1,3-dimethyl-5-cyclopentyloxypyrazol-4 -O-carboaldoxime-O-2-fluoro-3-(p-chlorophenyl)-2-propenyl ether and 1,3-dimethyl-5-(2,2,2-trifluoroethyloxy) pyrazol-4-carboaldoxime-O-2-fluoro-3-(p-chlorophenyl)-2-propenyl ether.

7. A heterocyclic compound of the formula:

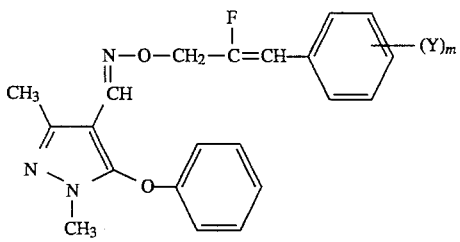

wherein Y is hydrogen, halogen, $C_1-C_4$ alkyl, $C_1-C_4$ haloalkyl, $C_1-C_4$ alkoxy or $C_1-C_4$ haloalkoxy; and m is an integer of 1 to 5.

8. A heterocyclic compound of the formula:

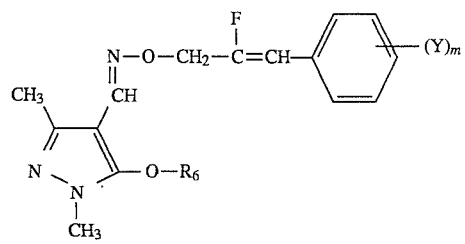

wherein $R_6$ is $C_1-C_{10}$ alkyl, $C_1-C_{10}$ haloalkyl, $C_2-C_{10}$ alkenyl, $C_2-C_{10}$ haloalkenyl, $C_2-C_{10}$ alkynyl, $C_2-C_{10}$ haloalkynyl, $C_1-C_4$ alkoxy $C_2-C_8$ alkyl, $C_1-C_4$ alkyl $C_2-C_8$ thioalkyl or $C_3-C_{10}$ cycloalkyl; Y is hydrogen, halogen, $C_1-C_4$ alkyl, $C_1-C_4$ haloalkyl, $C_1-C_4$ alkoxy or $C_1-C_4$ haloalkoxy; and m is an integer of 1 to 5.

9. A heterocyclic compound according to claim 8 wherein $R_6$ is $C_1-C_{10}$ alkyl or $C_3-C_{10}$ cycloalkyl.

10. A heterocyclic compound according to claim 7, which is 1,3-dimethyl-5-phenoxypyrazol-4-carboaldoxime-O-2-fluoro -3-(p-fluorophenyl)-2-propenyl ether.

11. A heterocyclic compound according to claim 7, which is 1,3-dimethyl-5-phenoxypyrazol-4-carboaldoxime-O-2-fluoro -3-(p-chlorophenyl)-2-propenyl ether.

12. A heterocyclic compound according to claim 7, which is 1,3-dimethyl-5-phenoxypyrazol-4-carboaldoxime-O-2-fluoro -3-phenyl-2-propenyl ether.

13. A heterocyclic compound according to claim 8, which is 1,3-dimethyl-5-cyclohexyloxypyrazol-4-carboaldoxime-O-2 -fluoro-3-(p-chlorophenyl)-2-propenyl ether.

14. A heterocyclic compound according to claim 8, which is 1,3-dimethyl-5-sec-butyloxypyrazol-4-carboaldoxime-O-2 -fluoro-3-(p-chlorophenyl)-2-propenyl ether.

15. An insecticidal, acaricidal and/or fungicidal composition which comprises as an active ingredient an insecticidally, acaricidally and/or fungicidally effective amount of a compound according to claim 1 or 2, and an inert carrier or diluent.

16. A method for controlling or exterminating insects acarids, and/or fungi which comprises applying as an active ingredient an insecticially, acaridally and/or fungicidally effective amount of a compound according to claim 1 or 2 to the locus where insects, acarids and/or fungi propagate.

* * * * *